United States Patent [19]
Penar

[11] 3,985,139
[45] Oct. 12, 1976

[54] COMBINATION BALLOON CATHETER AND EMERGENCY MEANS FOR DEFLATING THE BALLOON

[76] Inventor: Leonard J. Penar, 3623 W. Cermak Road, Chicago, Ill. 60623

[22] Filed: Aug. 25, 1975

[21] Appl. No.: 607,341

[52] U.S. Cl. .......................... 128/349 B; 81/15.4; 128/129; 128/246
[51] Int. Cl.² ...................................... A61M 25/00
[58] Field of Search ............. 81/15.4; 128/348–351, 128/325, 344, 246, 129

[56] References Cited
UNITED STATES PATENTS

| | | | |
|---|---|---|---|
| 1,664,621 | 4/1928 | Goff | 81/15.4 |
| 2,740,404 | 4/1956 | Kohl | 128/215 |
| 3,402,717 | 9/1968 | Doherty | 128/351 |
| 3,402,718 | 9/1968 | Doherty | 128/351 |
| 3,410,269 | 11/1968 | Hovick | 128/329 X |
| 3,726,283 | 4/1973 | Dye et al. | 128/349 BV |
| 3,825,013 | 7/1974 | Craven | 128/349 B |

*Primary Examiner*—Dalton L. Truluck
*Attorney, Agent, or Firm*—Kinzer, Plyer, Dorn & McEachran

[57] ABSTRACT

The combination of a balloon catheter; a thin flexible tube capable of insertion within the liquid drainage passage in the catheter; and a wire-like member capable of insertion through the flexible tube. The wire-like member has a sharpened end which can be used to pierce the catheter to deflate the balloon when it cannot be deflated in the normal manner.

8 Claims, 3 Drawing Figures

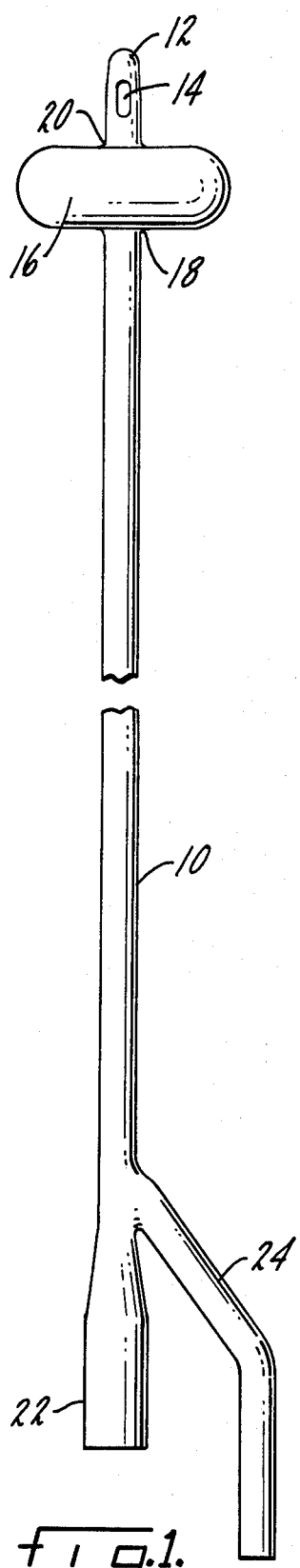
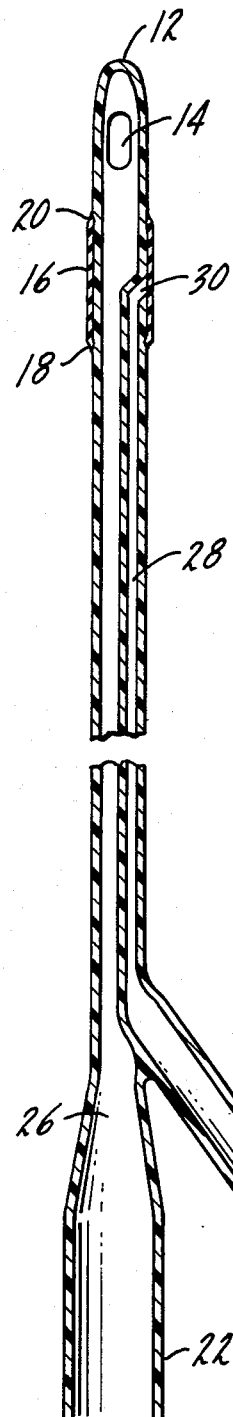
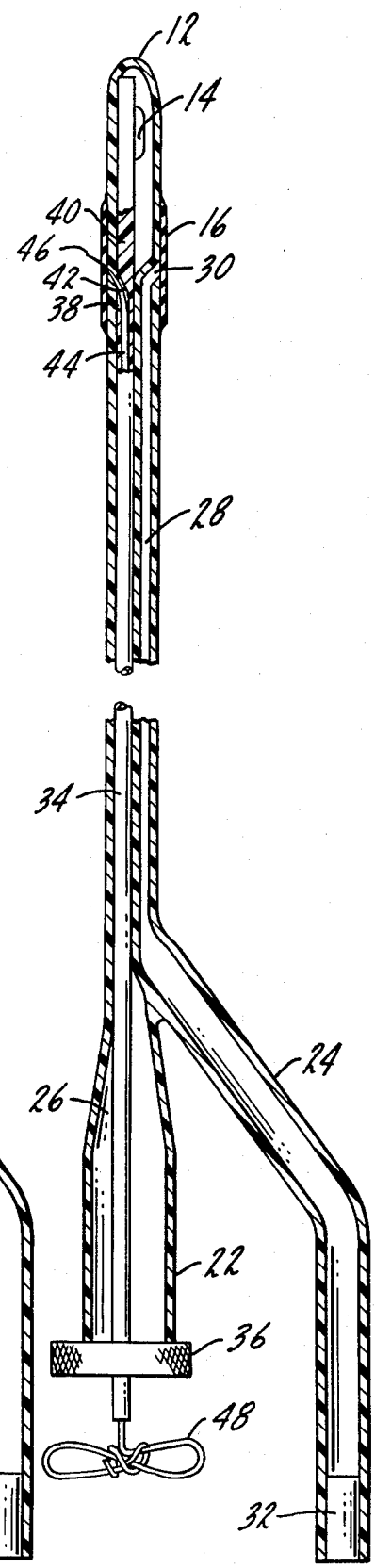

divergent tube 24 which
will be integrally formed with tubular member 10.

COMBINATION BALLOON CATHETER AND EMERGENCY MEANS FOR DEFLATING THE BALLOON

SUMMARY OF THE INVENTION

The present invention relates to urinary catheters and in particular to the combination of a catheter and means insertable within the catheter to deflate the balloon in an emergency situation.

A primary purpose of the invention is the combination of a balloon-type urinary catheter, a flexible tube for insertion through the drainage passage of the catheter, and a thin wirelike member for insertion through the tube to the point where it may be used to deflate the balloon within the patient's bladder.

Another purpose is a combination catheter and means for deflating the catheter balloon in an emergency situation.

Another purpose is a method of deflating a catheter balloon when the normal deflating means are inoperative.

Other purposes will appear in the ensuing specification, drawings and claims.

BRIEF DESCRIPTION OF THE DRAWINGS

The invention is illustrated diagrammatically in the following drawings wherein:

FIG. 1 is a plan view of a conventional urinary catheter showing the balloon in an inflated condition, FIG. 2 is a section through the catheter of FIG. 1 with the balloon in a deflated condition, and FIG. 3 is a section, similar to FIG. 2, showing the tube and wire for emergency balloon deflation positioned within the catheter.

DESCRIPTION OF THE PREFERRED EMBODIMENT

Typically, a balloon-type catheter is inserted through the urinary tract and into the patient's bladder. A balloon portion of the catheter is then inflated within the bladder, through the insertion of sterile fluid, to hold the catheter in place. At such time as the catheter is to be removed, the balloon portion is deflated by removal of the sterile fluid through the same passage which was used to inflate it. In rare instances the passage used to inflate and deflate the catheter balloon becomes blocked after the balloon is inflated and other means must be provided to deflate the balloon before the catheter can be removed from the patient. One such means for deflating the catheter balloon is shown in U.S. Pat. No. 3,825,013. The present invention provides for emergency catheter balloon deflation through the use of a thin flexible tube, for example a convenient plastic such as X-ray graduated woven nylon tubing, which is inserted through the drainage passage of the catheter to a point where an opening in the tube is generally adjacent the balloon within the patient's bladder. A wire is then inserted through the flexible tube and its sharpened point will pass through the opening in the flexible tube to a point where it may pierce the catheter adjacent the balloon within the patient's bladder, permitting subsequent deflation of the balloon and removal of the catheter.

The catheter may have an elongated flexible tubular member 10 terminating in an inner end 12 having drain openings 14. Spaced from and adjacent drain openings 14 is a balloon member 16 which extends about tubular member 10 and is secured thereto, by heat sealing, or by a suitable adhesive or the like, at its peripheral edges 18 and 20. The outer end of tubular member 10 may include a socket 22 which will conventionally fit about a glass or plastic tube and a divergent tube 24 which will be integrally formed with tubular member 10.

Looking particularly at FIG. 2, a first passage or main passage 26 is formed within tubular member 10 and is in communication with drain openings 14 and with socket 22. Conventionally, passage 26 will be used to drain fluids from within the patient's bladder or to provide a passageway to conduct irrigating fluids into the bladder. Also formed within tubular member 10 is a second passage 28 which has an opening 30 communicating with the interior surface of balloon member 16. Passage 28 extends through divergent tube 24 and may have its outer end closed by a small plug 32 which may be easily pierced by a hypodermic needle or the like.

In conventional catheter usage, the catheter is inserted through the urinary tract until the inner end having drain openings 14 is positioned within the patient's bladder. A syringe is inserted through plug 32 and a suitable sterile fluid is injected into passage 28 to expand or inflate balloon member 16 within the bladder, as illustrated in FIG. 1. The balloon is inflated to hold the catheter within the bladder. After inflation, passage 26 will be used in the conventional manner to drain the bladder or to provide a passageway for irrigating fluids.

At such time as it is desired to remove the catheter from the bladder, a syringe may again be inserted through plug 32 and is used to drain the sterile inflating fluid from passage 28 and from inside balloon member 16. As indicated above, there are rare occasions when passageway 28 becomes blocked. In such a situation, means must be provided to deflate the balloon, as otherwise removal of the catheter can be extremely painful and dangerous.

As particularly illustrated in FIG. 3, a thin hollow flexible tube 34 having a stop 36 at its outer end may be inserted into passage 26. Preferably, tube 34 may be formed of plastic, for example nylon or the like. Tube 34 has an opening 38 spaced a predetermined distance from its inner end, which opening is generally in alignment with balloon member 16 when tube 34 is fully inserted within catheter passage 26. The inner end of tube 34 may be closed, as indicated at 40, with the closure forming a ramp 42. After flexible tube 34 has been fully inserted in passage 26, with only stop 36 and a small portion of the tube remaining outside of the catheter, a thin wire-like member 44, which may be a steel wire, is inserted through the hollow interior of tube 34. Wire 44 has a sharpened inner end 46 and a stop 48 at its outer end. Wire 44 is inserted through the interior of tube 34 with ramp 42 causing the wire to bend outwardly and pass through opening 38 which is in alignment with balloon member 16. The wire will be pushed through tube 34 until its sharpened end 46 pierces tubular member 10, thus causing deflation of the balloon by dispersal of the sterile fluid into main passage 26. The distance which the wire can be inserted within the catheter must be closely controlled so as to not injure the patient. Stop 48 is used as a guide to determine when the proper length of wire has been inserted within the catheter. Thus, the length of wire 44 and the length of flexible tube 34 are slightly longer than passage 26 so that the wire and tube may be inserted to perform their intended function, but leave a gripping area on the exterior of the catheter for manipulation by the doctor or nurse who is performing the balloon deflating operation.

Flexible tube 34 should be formed of a material which is readily deformable to the shape of the urinary tract so that it may be passed through the catheter without causing excessive discomfort to the patient. In like manner, wire 44 must be sufficiently flexible to pass through the same passage, but yet be sufficiently stiff to provide a sharpened cutting point on its end which can be used to pierce the catheter and deflate the balloon within the patient's bladder. Plastic has been found to be satisfactory for tube 34 and a steel wire has been found to be satisfactory for wire 44, although other materials may be equally applicable.

Whereas the preferred form of the invention has been shown and described herein, it should be realized that there may be many modifications, substitutions and alterations thereto.

The embodiments of the invention in which an exclusive property or privilege is claimed are defined as follows:

1. In combination, a balloon catheter including an elongated flexible tubular member terminating in an inner end having drain openings, a first passage in said tubular member in communication with said drain openings at said inner end and terminating at its outer end in an enlarged opening, an inflatable balloon member attached to the exterior of said tubular member adjacent said drain openings, a second passage in said tubular member communicating with said balloon member for inflating and deflating said balloon member, a flexible tube of a size and shape for insertion in said first passage and having a length at least equal to that of said first passage, an opening adjacent one end of said flexible tube, which opening is generally in alignment with said balloon member when said flexible tube has been fully inserted in said first passage, and a thin flexible wire-like member of a size and shape to be inserted in said flexible tube and having a length at least sufficient to extend through said flexible tube and through said opening, said flexible wire-like member having a sharpened end for use in piercing said tubular member, after passing through said flexible tube opening.

2. The combination of claim 1 further characterized by and including a stop on the outer end of said flexible tube for preventing insertion of said flexible tube in said first passage beyond a predetermined length.

3. The combination of claim 2 further characterized by and including a stop on the outer end of said wire-like member for preventing insertion of said wire-like member beyond a predetermined length.

4. The combination of claim 2 further characterized in that said flexible tube is formed of a plastic material.

5. The combination of claim 3 further characterized in that said wire-like member is a metallic wire having a sharpened end.

6. The combination of claim 1 further characterized by and including ramp means within said flexible tube adjacent the inner end thereof and adjacent said opening for causing said wire-like member to be directed outwardly through said opening.

7. A method of deflating the balloon of a balloon catheter inserted within a human body when normal deflating means are inoperative said catheter having an annular wall defining a drain passage with a balloon member adjacent the insertion end of the catheter, said method comprising the steps of:
 a. inserting a flexible tube having an opening adjacent one end into the catheter drain passage until the tube opening is positioned in general alignment with the catheter inflated balloon,
 b. inserting a wire-like member having a sharpened end through said flexible tube until the wire passes through said tube opening and pierces the catheter wall causing deflation of the balloon.

8. The method of claim 7 further characterized by the step of limiting insertion of said wire-like member to the distance generally necessary for piercing the catheter.

* * * * *